US009763976B1

United States Patent
Obagi et al.

(10) Patent No.: US 9,763,976 B1
(45) Date of Patent: Sep. 19, 2017

(54) COMPOSITION AND METHOD FOR TREATING SKIN CONDITIONS

(71) Applicant: ZO SKIN HEALTH, INC., Irvine, CA (US)

(72) Inventors: Zein E. Obagi, Irvine, CA (US); Frederick W. Woodin, Jr., Irvine, CA (US)

(*) Notice: Subject to any disclaimer, the term of this patent is extended or adjusted under 35 U.S.C. 154(b) by 0 days.

(21) Appl. No.: 15/226,349

(22) Filed: Aug. 2, 2016

(51) Int. Cl.

| | |
|---|---|
| A61K 8/35 | (2006.01) |
| A61K 8/37 | (2006.01) |
| A61K 8/42 | (2006.01) |
| A61K 8/60 | (2006.01) |
| A61K 8/64 | (2006.01) |
| A61K 8/66 | (2006.01) |
| A61K 8/73 | (2006.01) |
| A61K 9/00 | (2006.01) |
| A61K 31/045 | (2006.01) |
| A61K 31/047 | (2006.01) |
| A61K 31/19 | (2006.01) |
| A61K 31/702 | (2006.01) |
| A61Q 17/04 | (2006.01) |
| A61P 17/00 | (2006.01) |
| A61K 31/78 | (2006.01) |
| A61K 31/7016 | (2006.01) |
| A61K 38/02 | (2006.01) |
| A61K 31/197 | (2006.01) |
| A61K 31/734 | (2006.01) |
| A61K 31/225 | (2006.01) |
| A61K 8/34 | (2006.01) |
| A61K 31/22 | (2006.01) |
| A61K 36/47 | (2006.01) |
| A61K 8/92 | (2006.01) |
| A61K 8/85 | (2006.01) |
| A61K 31/745 | (2006.01) |
| A61K 8/81 | (2006.01) |
| A61K 38/48 | (2006.01) |
| A61K 8/19 | (2006.01) |

(52) U.S. Cl.
CPC ............... *A61K 31/78* (2013.01); *A61K 8/19* (2013.01); *A61K 8/342* (2013.01); *A61K 8/345* (2013.01); *A61K 8/37* (2013.01); *A61K 8/42* (2013.01); *A61K 8/60* (2013.01); *A61K 8/64* (2013.01); *A61K 8/66* (2013.01); *A61K 8/733* (2013.01); *A61K 8/8105* (2013.01); *A61K 8/85* (2013.01); *A61K 8/922* (2013.01); *A61K 9/0014* (2013.01); *A61K 31/045* (2013.01); *A61K 31/047* (2013.01); *A61K 31/197* (2013.01); *A61K 31/22* (2013.01); *A61K 31/225* (2013.01); *A61K 31/7016* (2013.01); *A61K 31/734* (2013.01); *A61K 31/745* (2013.01); *A61K 36/47* (2013.01); *A61K 38/02* (2013.01); *A61K 38/4873* (2013.01); *A61Q 17/04* (2013.01); *A61K 2800/48* (2013.01); *A61K 2800/51* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 8,778,336 B2 | 7/2014 | Chavan | |
| 2005/0089499 A1* | 4/2005 | Moussou | ................. A61K 8/97 424/74 |
| 2011/0177052 A1 | 7/2011 | Chavan | |

OTHER PUBLICATIONS

Rimmerman et al., Molecular Pharmacology (2008), pp. 213-224.*
Sesquiterpenes (2016), pp. 1-8.*
Cosmetic Ingredient Review (2017), Safety Assessment of Panthenol, Pantothenic Acid, and Derivatives as Used in Cosmetics.*
"Distinctive Phytostem Edelweiss", Resources of Nature, Inc., 2 pages, rev. Oct. 19, 2010.
Barnet, "Neurocap", SynAging, 32 pages, Apr. 2015.
Daniela et al., "Anti-Inflammatory Effects of Concentrated Ethanol Extracts of Edelweiss (*Leontopodium alpinum* Cass.) Callus Cultures towards Human Keratinocytes and Endothelial Cells", Mediators of Inflammation, vol. 2012, Article ID 498373, 12 pages, (2012).
"Modukine", CLR—Chemisches Laboratorium Dr. Kurt Richter GmbH, 16 pages, (2012).
"X-pressin, the rapid healthy glow-enhancing technology for the finishing touches that can make you look more beautiful after just one use!", BASF Beauty Care Solutions, 4 pages, (2010).
"Unitrienol T-27 and T-272 WSL: Hair and Skin Sebum Normalizer", Induchem AG, TDS Unitrienol Version 07, 19 pages, Jul. 31, 2014.
"Timecode: In vitro and ex vivo evaluation of its anti-ageing activity", Seppic, 37 pages, Oct. 3, 2008.

* cited by examiner

*Primary Examiner* — John Pak
*Assistant Examiner* — Frank Choi

(57) ABSTRACT

Provided are biocompatible topical compositions including a novel combination of an inflammatory management agent, a vascular repair agent, a neurogenic agent, a sebum suppression agent and an exfoliating agent. Also provided are methods for treating, preventing or ameliorating rosacea, a symptom thereof or a condition related thereto by administering the biocompatible topical compositions describe herein.

20 Claims, 2 Drawing Sheets

Baseline—Patient 4    Week 6

Baseline—Patient 1    Week 6

COMPOSITION AND METHOD FOR TREATING SKIN CONDITIONS

FIELD

The present subject matter relates to biocompatible topical compositions and methods of treating rosacea by administering the same.

BACKGROUND

Rosacea is a chronic skin condition characterized by recurrent episodes of flushing, erythema, vasodilation, telangiectasia, edema, papules, pustules, hyperplasia, fibroplasia, itching, burning, pain, and skin tightness. Symptoms of rosacea are exacerbated by sun exposure, hot weather, immersion in hot water, high humidity, sweating, exercise, emotional stress, and spicy food.

The etiology of rosacea is not well understood. Furthermore, treatments, including, for example, antibiotic administration, topical drugs and known cosmetics may yield only marginal improvement. In addition, such treatments have been known to aggravate rosacea rather than alieve it. For example, in a National Rosacea Society survey of 1,066 patients, 41 percent reported that certain skin-care products aggravated their condition and 27 percent said certain cosmetics also caused rosacea flare-ups.

Therefore, there is a need to identify compositions that can be used to treat, prevent or ameliorate rosacea, symptoms thereof and conditions related thereto, especially compositions that do not aggravate the rosacea or symptoms associated therewith.

SUMMARY

The present subject matter relates to topical compositions and methods for treating rosacea including administering a topical composition.

More specifically, provided is a biocompatible topical composition comprising or consisting of a novel combination of an inflammatory management agent, a vascular repair agent, a neurogenic agent, a sebum suppression agent and an exfoliating agent for treating, preventing and/or stabilizing Rosacea conditions and symptoms thereof or a condition related thereto.

The topical composition may optionally comprise or consist of one or more additional agents. For example, the topical composition may optionally comprise or consist of a carrier, which may be a solvent, a chelating agent, a humectant, a thickener, an emollient, an emulsifier, a skin conditioning agent, an anti-inflammatory agent, an antioxidant, a pH adjuster and/or a preservative. In addition, the topical composition may also comprise or consist of one or more biocompatible carrier, excipient, filler and/or diluent.

Also provided is a rosacea treatment, prevention or amelioration skin kit. The skin kit may comprise or consist of the topical composition provided herein and one or more additional composition. The one or more additional composition may be a skin cleanser, an oral composition for treating skin, a sunscreen such as, e.g., an organic sunscreen, a moisturizing composition, an exfoliating composition such as, e.g., an exfoliating polish, a barrier protecting composition and/or an additional topical composition for treating, preventing or ameliorating rosacea, a symptom thereof or a condition related thereto such as, e.g., a topical formulation comprising salicylic acid or benzoyl peroxide. The kit may also include a device for concomitant therapy. Additionally the kit may include one or more topical or oral homeopathic composition. The kit may further include instructions for use and packaging.

The presently described subject matter also relates to a method of treating, preventing or ameliorating rosacea or a symptom thereof in a subject, comprising or consisting of topically administering to the subject a therapeutically effective amount of the biocompatible topical composition described herein.

DETAILED DESCRIPTION

Definitions

Figure 1:
FIG. 1 shows a side-by-side photographic comparison of a patient suffering from rosacea prior to and following six weeks of regular administration of the topical compositions described herein.

The term "about" as used herein refers to a quantity, level, value, dimension, size, or amount that varies to some extent based on the context in which it is used. For example, such variation can be by as much as 5%. At the least, each numerical parameter can be construed in light of the number of reported significant digits and by applying ordinary rounding techniques.

As used herein, the terms "administer," "administering," and "administration," refer to any method which, in sound medical practice, delivers the composition to a subject in such a manner as to provide a therapeutic effect.

For the purposes of the presently described subject matter, the present topical biocompatible compositions can be topically administered. For example, administration can include, but is not limited to, direct topical administration. For example, a viscous formulation, including for example a cream, gel, ointment, or salve formulation, or a liquid formulation, for example, a solution, can be administered directly to a desired skin surface. Administration can also be accomplished via a compress or a wet dressing. For example, a liquid, e.g., solution, emulsion, suspension, etc., formulation of the presently described topical composition can be applied to a skin surface via a compress or wet dressing.

As used herein, the phrases "anti-inflammatory agent" and "inflammatory management agent" refer to a compound or composition capable of preventing, reducing or ameliorating inflammation. Non-limiting examples of inflammatory management agents include, e.g., lactose and milk protein, or a combination thereof. Anti-inflammatory agent may also refer to, for example a chemical compound, that acts to reduce one or more indications of inflammation, such indications including, but not limited to, swelling, redness, tenderness, and pain. Such compounds can include but are not limited to Beta Glucan, *Avena Sativa* (Oat) Kernel Meal, *Avena Sativa* (Oat) Kernal Protein USP, *Avena sativa* (Oat) Kernal Flour, whey protein concentrates, and combinations thereof.

The term "antioxidant" refers to an atom, molecule, or a compound that inhibits the oxidation of other molecules, has a greater oxidation potential than a second atom or molecule, such that the antioxidant is preferentially oxidized instead of the second atom or molecule. For example, an antioxidant can have a greater oxidation potential than hematein, and thus help prevent oxidation of hematein to oxyhematein. Furthermore, an antioxidant also can function as a reducing agent, for example, a reducing agent that converts oxyhematein back to hematein. Antioxidants can be present in the disclosed compositions at concentrations ranging from about 1 mM to about 1M, for example, from about 5 mM to about 500 mM, such as from about 50 mM to about 150 mM. Antioxidants serve to neutralize the deleterious effects of reactive oxygen species and/or free radicals that can be generated by various internal and external stimuli within human tissue.

Non-limiting examples of antioxidants include one or more of *Leontopodium Alpinum* Meristem Cell Culture, *Marrubium Vulgare* Meristem Cell Culture (e.g., DISTINCTIVE® Phytostem Edelweiss), Tocopheryl Acetate, Ascorbic Acid and/or Retinyl Palmitate, soluble soy protein, Idebenone, coenzyme Q10, Lycopene, Epigallocatechin 3-gallate (EGCG), green tea polyphenols (GTP), Silymarin, CoffeeBerry®, Grape seed extract, Pomegranate extracts, Genistein, pycnogenol, niacinamide, methionine, glutathione, tocotrienol, dimethyl glycine, betaine, butylated hydroxyanisole, butylated hydroxytoluene, turmerin, vitamin E, ascorbyl palmitate, deteroxime mesylate, methyl paraben, ethyl paraben, butylated hydroxyanisole, butylated hydroxytoluene, propyl gallate, sodium or potassium metabisulfite, sodium or potassium sulfite, alpha tocopherol or derivatives thereof, sodium ascorbate, disodium edentate, BHA (butylated hydroxyanisole), flavonoids, a pharmaceutically acceptable salt or ester of the mentioned compounds, and mixtures thereof. Flavonoids include, for example, quercetin, morin, naringenin and hesperetin, taxifolin, afzelin, quercitrin, myricitrin, genistein, apigenin and biochanin A, flavone, flavopiridol, isoflavonoids such as the soy isoflavonoid, genistein, catechins such as the tea catechin epigallocatechin gallate, flavonol, epicatechin, hesperetin, chrysin, diosmin, hesperidin, luteolin, and rutin.

The term "biocompatible" or "physiologically compatible," as used herein, refers to the ability to be in contact with a living system without producing a significant adverse effect, for example, by not being toxic, injurious, or physiologically reactive.

As used herein, the phrases an "effective amount" or a "therapeutically effective amount" of a composition and/or active agent or ingredient, which are synonymous herein, refer to an amount of the active agent sufficient enough to have a therapeutic effect upon administration. A therapeutically effective amount of the active agent may, will, or is expected to cause a relief of symptoms. Effective amounts of the active agent will vary with the particular condition or conditions being treated, the severity of the condition, the duration of the treatment, the specific components of the composition being used, and like factors. For example, the presently described compositions can be topically applied in an amount sufficient to cover an affected area. The presently described compositions can be topically applied in an amount sufficient to cover an affected area plus a margin of healthy skin or tissue surrounding the affected area, for example, a margin of about 0.5 inches.

"Chelating agent," as used herein refers to an agent, e.g., a chemical, capable of removing a metal ion from a system by forming a complex so that the metal ion cannot readily participate in or catalyze chemical reactions. Non-limiting examples of chelating agents include, for example, one or more of citric acid, phosphates, disodium EDTA, tetrasodium EDTA, ethylene glycol-bis-(b-aminoethylether)-N,N, N',N'-tetraacetic acid (EGTA), 1,2-bis(2-aminophenoxy) ethane-N,N,N',N'-tetraacetic acid (BAPTA); ethylene-N, N'-diglycine (EDDA), 2,2'-(ethylendiimino)-dibutyric acid (EBDA), lauroyl EDTA, dilauroyl EDTA, triethylene tetramine dihydrochloride (TRIEN), diethylenetriamin-pentaacetic acid (DPTA), triethylenetetramine hexaacetic acid (TTG), deferoxamine, Dimercaprol, zinc citrate, penicilamine succimer, Editronate, and edetate calcium disodium.

As used herein the term "emollient" refers to any product applied to the skin which softens and/or soothes irritation of the skin, including, for example, ointments, liniments, lotions, creams, moisturizers, oils, skin softeners, soaps, shampoo, sunscreens, cosmetics and the like. Non-limiting examples of emollients suitable for the biocompatible topical compositions herein include, for example, one or more of *Aleurites* Moluccan Seed Oil, Carthamus Tinctorius (Safflower) Seed Oil, Isohexadecane, Methylheptyl Isostearate, Neopentyl Glycol Diethylhexanoate, Neopentyl Glycol Diisostearate and/or C12-15 Alkyl Benzoate, Hydrogenated Polyisobutene, C-12-C-15 alcohols benzoate, isopropyl myristate, mineral oils, lanolin and lanolin derivatives, and triglycerides such as coconut oil, cetostearyl alcohol, cetyl alcohol, isopropyl palmitate, caprylic/capric triglyceride, PPG-2 myristyl ether propionate, dimethicone, methicone, petrolatum, lanolin, and mineral oil.

As used herein "emulsifier" refers to a compound or substance at acts as a stabilizer for emulsions preventing the liquids from separating. Non-limiting examples of emulsifiers suitable for the present biocompatible topical compositions include, for example one or more of PEG-100 Stearate, PEG-15/Lauryl Dimethicone Crosspolymer, Polyglyceryl-4 Isostearate and/or Cetyl PEG/PPG 10/1 Dimethicone and/or Hexyl Laurate, polyoxyethylene fatty ethers derived from stearyl alcohols, Isopropyl Isostearate, Cetyl Alcohol, polyethylene glycol stearate, a glycol stearate, a glyceryl stearate, cetearyl alcohol, ceteareth 20, methylcellulose, cetomacrogol 1000, and lecithin.

The term "humectant" refers to a substance capable of reducing the loss of moisture. Non-limiting examples of humectants include, for example, glycerin, sodium hyaluronate, glycerin, glycerol, propylene glycol, glyceryl triacetate, a lanolin product, such as PPG-12-PEG 50, polyhydric alcohols, water soluble alkoxylated nonionic polymers, and mixtures thereof. Polyhydric alcohols useful herein include glycerin, sorbitol, propylene glycol, butylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. Commercially available humectants herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

As used herein, the phrase "exfoliating agent" refers to any mechanical, chemical or naturally derived agent that is applied to the skin to accelerate the removal of dead cells from the skin surface to relive dry skin, assist removal of papules or pustules, and/or reducing wrinkles. The exfoliating agent may include at least one plant derived cysteine protease enzyme.

Suitable exfoliating agents may include one or more proteases including, e.g., papain, bromelain, protease, serrapeptase, chymotrypsin, trypsin, fungal protease, amylase, plasmin, fibrinolysin, ficin, snake venom proteases, and peptidase. The protease may be alone or in combination with other agents. For example the exfoliating agent may be a combination of one or more of a carbomer, Papain, 1,2 Hexanediol, Caprylyl Glycol and Algin. An example of an exfoliating agent that includes all of the aforementioned agents is X-PRESSIN C manufactured by BASF. Other combinations may be found, e.g., in US Patent Application Publication No. 20110177052 and U.S. Pat. No. 8,778,336, which are incorporated herein by reference in their enterits.

"Neurogenic agent," as used herein, refers to any agent capable of treating preventing, or ameliorating inflammation or other conditions arising from the local release of inflammatory mediators from afferent neurons such as, for example, Substance P, Calcitonin Gene-Related Peptide (CGRP), neurokinin A (NKA), and/or endothelin-3 (ET-3). Sensory as well as autonomic (sympathetic) nerves influence a variety of Physiological and Pathophysiological functions within the skin such as vasocontraction/vasoldilation, inflammation and barrier function. Autonomous nerves in skin, mainly sympathetic cholinergic innervate several cells in the skin are responsible for maintaining skin homeostasis and regulating inflammation. A dense network of sensory nerves in skin also release neuropeptides, thereby modulating inflammation, cell growth, as well as immune responses in the skin. Neurodegeneration in skin causes a loss of homeostatic control over these various biological functions in human skin. It is further understood that:
  neurovascular issues affect both nerves and blood vessels;
  subepidermal afferent nerves are involved in the reflex activation of sweat glands;
  prominent flushing may be attributed to abnormalities in neurovascular homeostasis; and
  over production of inflammatory inducing Reactive Oxygen Species is also a central feature of all Neurodegenerative disorders.

With aging, neurons (among them cutaneous neurons) degenerate, especially in the dermis, where fibroblasts and neurons are continuously communicating. A neurogenic agent is capable of protecting nerve endings and/or maintains healthy communications between nerves and fibroblasts.

Suitable neurogenic agents in the present compositions include, for example, one or more of hydrolyzed algin (alone or with water), substance P antagonists, extracts of at least one non-photosynthetic filamentous bacterium, CGRP antagonists, NO-synthase inhibitors, bradykinin antagonists, cytokine antagonists, histamine antagonists, antagonists of interleukin-1 and/or of tumor necrosis factor α (TNF-α), sodium-channel blockers and potassium-channel openers.

NEUROCAP (available from Codif/Barrnet) is a preferred neurogenic agent for use in the compositions described herein. NEUROCAP is an oligosaccharide mainly composed of 2 uronic acids (guluronic and mannuronic) obtained by enzymatic depolymerization from saccharides coming from brown algae. NEUROCAP includes water and hydrolyzed algin.

As used herein the terms "pH adjuster" and "neutralizing agent" refer to any composition, compound, or agent, suitable for adjusting the pH of the presently described topical compositions without negatively affecting any property thereof. Suitable pH adjusters can include any acid or base. Suitable pH adjusters can include but are not limited to one or more of sodium hydroxide, aminomethyl propanol, hydrochloric acid, sulfuric acid, citric acid, acetic acid, formic acid, phosphoric acid, tartric acid, and triethanolamine.

"Solvent" or "carrier" refers to inorganic and/or organic molecules and compounds capable of at least partially dissolving another substance (i.e., the solute). Solvents may be liquids at room temperature. Non-limiting examples of solvents include, for example, one or more of water, deionized water, hydrocarbon solvents (e.g., n-pentane, n-hexane, n-heptane, n-octane, paraffin, cyclohexane, methylcyclohexane, decahydronaphthalene, mineral oil, crude oils, etc.) which also includes aromatic hydrocarbon solvents (e.g., benzene, toluene, o-xylene, m-xylene, and p-xylene), halogenated hydrocarbon solvents (e.g., carbon tetrachloride, 1,2-dichloroethane, dichloromethane, chloroform, etc.), ester solvents (e.g., ethyl formate, methyl acetate, ethyl acetate, ethyl malonate, etc.), ketone solvents (e.g., acetone, methyl ethyl ketone, cyclohexanone, cyclopentanone, etc.), ether solvents (e.g., diethyl ether, dipropyl ether, diphenyl ether, tetrahydrofuran, 1,4-dioxane, etc.), amine solvents (e.g., propyl amine, diemylamine, triethylamine, aniline, pyridine), alcohol solvents (e.g., methanol, ethanol, 1-propanol, 1-butanol, 1-octanol, benzyl alcohol, trifluoroethanol), glycol solvents (glycerol, ethylene glycol, propylene glycol, m-cresol, etc.), acid solvents (e.g., acetic acid, hexanoic acid, etc.), carbon disulfide, nitrobenzene, N,N-dimethylformamide, N,N,-dimethylacetam ide, dimethyl sulfoxide, N-methyl-2-pyrrolidone, acetonitrile, silicone solvents (e.g., silicone oils, polysiloxanes, cyclosilicones). A preferred solvent in the present compositions is water.

As used herein, "skin conditioning agent" or refers to any material capable of protecting, treating compromised skin. Non-limiting examples of skin conditioning agents include one or more of allantoin, aluminium hydroxide gel, calamine, cocoa butter, cod liver oil, cyclopentasiloxane, dimethicone, dimethicone crosspolymer, dimethiconol, glycerine, kaolin, petrolatum, lanolin, mineral oil, shark liver oil, white petrolatum, talc, topical starch, zinc acetate, zinc carbonate, zinc oxide, live yeast cell derivatives, aldioxa, aluminum acetate, microporous cellulose, cholecalciferol, colloidal oatmeal, cysteine hydrochloride, dexpanthenol, protein hydrolysates, racemic methionine, sodium bicarbonate, vitamin A, buffered mixture of cation and anion exchange resins, corn starch, trolamine, bismuth subnitrate, boric acid, ferric chloride, polyvinylpyrrolidone-vinyl acetate, copolymers, sulfur, tannic acid, derivatives thereof and mixtures thereof.

As used herein, the term "salt" refers to salts of certain ingredient(s) which possess the same activity as the unmodified compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

As used herein the term "preservative" refers to any known biocompatible preservative that functions by inhibiting bacteria and/or fungi, and/or by inhibiting oxidation. Suitable preservatives can include but are not limited to antimicrobial agents and/or antioxidants. Suitable antimicrobial agents as preservatives can include but are not limited to benzoates, benzyl alcohol, sodium benzoate, n-alkyl dimethyl benzyl ammonium chloride, Caprylyl Glycol, Chlorphenesin, methylparaben, propylparaben, ethylhexylglycerin, phenoxyethanol, Phenoxyethanol and Caprylyl Glycol and Chlorphenesin, chlorocresol, potassium sorbate, sorbic acid, bronopol, methychloroisothiazolinone, methylisothiazolinone, sorbates, propionates, and nitrites. Suitable antioxidants can include but are not limited to vitamin C, butylated hydroxytoluene (BHT), sulphites, and vitamin E.

The phrase "sebum suppression agent," as used herein, refers to any agent capable of decreasing the production of sebum by the sebaceous glands. Nonlimiting examples of sebum suppression agents include, for example, ASEBIOL (available from Laboratories Serobiologiques), BIODERMINE (available from Sederma), COMPLETECH MBAC-OS (available from Lipo), cucumber extracts, dehydroacetic acid and its salts, dichlorophenyl imidazoldioxolan, niacinamide, phloretin, PHLOROGINE (available from Secma), S-carboxylmethyl cysteine, tioxolone, tocopherol, UNITRIENOL T27, which includes Panthenyl Triacetate, Farnesol and Farnesyl Acetate (available from Induchem), UNITRIENOL, which includes PEG-12 Glyceryl Laurate, PEG-36 Castor Oil, Panthenyl Triacetate, Farnesol and Farnesyl Acetate (available from Induchem) and mixtures thereof.

As used herein, "symptom" refers to an indication of disorder or disease, especially when experienced by an individual as a change from normal function, sensation, or appearance. See "symptom". The American Heritage® Science Dictionary. Houghton Mifflin Company. A symptom may also be referred to as a "sign."

Non-limiting examples of symptoms of rosacea include, for example, erythema, telangiectasia, abnormal skin texture, skin discoloration, excess sebum production, swelling of the skin, skin nodularities, red patches on the skin, desquamation, skin lesions, stinging/burning, flushing and/or dry/tight skin.

The phrase "substantially pure" as used herein refers to an individual compound form, which is substantially devoid of all other forms, as well as degradation products of a form, and any residual solvent, and is at least 85% pure on a % weight basis, unless otherwise specified. The compound form can have at least 90% purity on a % weight basis, at least 93% purity on a % weight basis, at least 95% purity on a % weight basis, or at least 97% purity on a % weight basis. As used herein substantially pure may refer to food grade ingredients used in topical compositions.

As used herein, "subject" or "individual" or "animal" or "patient" or "mammal," refers to any subject, particularly a mammalian subject, for whom diagnosis, prognosis, or therapy is desired, for example, a human.

As used herein, "thickener" or "thickening agent" refers to any agent useful as an aid to thicken or add structure to a topical formulations. These agents impart physical stability and increased viscosity. Additionally, a thickener refers to one or more agents that, in combination, result in a viscosity suitable for dermatologic applications. Thickening agents herein may be, for example, gums and natural polysaccharides, mineral thickeners, oils, and synthetic polymeric thickeners. Non limiting examples of thickeners suitable for use in the present topical compositions include, for example, one or more of Xanthan Gum, Cetyl Alcohol, PEG-100 Stearate, Glyceryl Stearate, and Magnesium Aluminum Silicate.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. In this regard, treatment may include treating, preventing or ameliorating a disease, a symptom thereof or a condition related thereto. A useful composition herein needs only to reduce the severity of a disease, disorder, or condition, reduce the severity of symptoms associated therewith, provide improvement to a patient or subject's quality of life, or delay or inhibit the onset of a disease, disorder, or condition.

The phrase "vascular repair agent" refers to an agent, i.e., a compound or composition, capable of healing and/or restructuring of the skin including, for example, promotion of neovascularization, which leads to a restoration of blood flow. Non-limiting examples of vascular repair agents include, for example, water-soluble vitamins such as palmitoyl glycine, vitamin A or derivatives thereof, vitamin E or derivatives thereof, N-acetyl-hydroxyproline, extracts of *Centella asiatica* and of dill, papain, the essential oils of thyme, of niaouli, of rosemary and of sage, hyaluronic acid, allantoin, Héma'tite® (Gattefossé), vitamin C, TECO® Pep 4-17 (Evonik), Toniskin® (Silab), Collageneer® (Expanscience), TIMECODE®, which includes Palmitoyl Glycine (Seppic), GATULINE® skin repair (Gattefossé), panthenol, PHYTOCELTEC Alp Rose (MibelleBiochemistry), Serilesine® (Lipotec), heterosides of Talapetraka (Bayer), STOI- CHIOLI® (Codif), macarose (Sensient), DERMAVEIL (Ichimaru Pharcos), Phycosaccharide AI (Codif) and/or metformin.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application. For example, "an" astringent component refers to both one astringent component or a mixture comprising two or more astringent components.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained.

Throughout the application, descriptions of various embodiments use "comprising" language; however, it will be understood by one of skill in the art, that in some specific instances, an embodiment can alternatively be described using the language "consisting essentially of" or "consisting of."

Other terms as used herein are meant to be defined by their well-known meanings in the art.

Biocompatible Topical Compositions

The presently described biocompatible topical compositions can be provided in any form, including, but not limited to a gel, a cream, a lotion, an ointment, a foam, an aerosol, a powder, a solution, an emulsion, and a serum.

The biocompatible topical compositions described herein may include an inflammatory management agent.

The topical compositions may comprise one or more anti-inflammatory or inflammatory management agents as described and defined above. The anti-inflammatory or inflammatory management agent may be present in the topical compositions in an amount of from >0.01 wt. % to about 12.5 wt. %; from >0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 12.5 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more vascular repair agents as described and defined above. The vascular repair agent may be present in the topical compositions in an amount of from >0.01 wt. % to about 15 wt. %; from >0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more neurogenic agents as described and defined above. The neurogenic agent may be present in the topical compositions in an amount of from >0.01 wt. % to about 22.5 wt. %; from >0.01 wt. % to about 15 wt. %; from >0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 22.5 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt.

% to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more sebum suppression agents as described and defined above. The sebum suppression agent may be present in the topical compositions in an amount of from >0.01 wt. % to about 25 wt. %; from >0.01 wt. % to about 15 wt. %; from >0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 25 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more exfoliating agents as described and defined above. The exfoliating agent may be present in the topical compositions in an amount of from >0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more carrier/solvents as described and defined above. The carrier/solvent may be present in the topical compositions in an amount of from about 30 wt. % to about 90 wt. %; from about 40 wt. % to about 80 wt. %; from about 40 wt. % to about 50 wt. %; 45 wt. % to about 47 wt. %; from about 60 wt. % to about 80 wt. %; from about 65 wt. % to about 75 wt. %; from about 67 wt. % to about 73 wt. %; about 46%, about 70% or about 72 wt. %; or in any other amount within any of the above ranges.

The topical compositions may also include one or more chelating agents as described and defined above. The chelating agent may be present in the present compositions in an amount of from <0.01 wt. % to about 5 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 5 wt. %; or in any other amount within any of the above ranges.

The topical compositions may also include one or more humectants as described and defined above. The humectant may be present in the topical compositions in an amount of from <0.01 wt. % to about 15 wt. %; from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more thickeners as described and defined above. The thickener may be present in the topical compositions in an amount of from <0.01 wt. % to about 30 wt. %; from <0.01 wt. % to about 20 wt. %; from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 30 wt. %; from 0.25 wt. % to about 25 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more emollients as described and defined above. The emollient may be present in the topical compositions in an amount of from <0.01 wt. % to about 30 wt. %; from <0.01 wt. % to about 20 wt. %; from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 30 wt. %; from 0.25 wt. % to about 25 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more emulsifiers as described and defined above. The emulsifier may be present in the topical compositions in an amount of from <0.01 wt. % to about 40 wt. %; from <0.01 wt. % to about 20 wt. %; from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 40 wt. %; from 0.25 wt. % to about 30 wt. %; from 0.25 wt. % to about 25 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical compositions may also include one or more skin conditioning agents as described and defined above. The skin conditioning agent may be present in the topical compositions in an amount of from <0.01 wt. % to about 60 wt. %; from <0.01 wt. % to about 20 wt. %; from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 50 wt. %; from 0.25 wt. % to about 30 wt. %; from 0.25 wt. % to about 25 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; from about 3 wt. % to about 10 wt. %; or in any other amount within any of the above ranges.

The topical composition may also include one or more antioxidant as described and defined above. The antioxidant may be present in the topical compositions in an amount of from <0.01 wt. % to about 30 wt. %; from <0.01 wt. % to about 20 wt. %; from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 30 wt. %; from 0.25 wt. % to about 25 wt. %; from 0.25 wt. % to about 20 wt. %; from 0.25 wt. % to about 15 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; or in any other amount within any of the above ranges.

The topical compositions may also include one or more pH adjusters as described and defined above. The pH adjuster may be present in the topical compositions in an amount of from <0.01 wt. % to about 3 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 3 wt. %; from 1 wt. % to about 2.5 wt. %; from 1 wt. % to about 2.25 wt. %; from 1 wt. % to about 2 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; or in any other amount within any of the above ranges.

The topical compositions may also include one or more preservatives as described and defined above. The preservative may be present in the present compositions in an amount of from <0.01 wt. % to about 10 wt. %; from 0.01 wt. % to about 9 wt. %; from 0.01 wt. % to about 8 wt. %; from 0.01 wt. % to about 7 wt. %; from 0.01 wt. % to about 6 wt. %; from 0.01 wt. % to about 5 wt. %; from 0.01 wt. % to about 4.5 wt. %; from 0.01 wt. % to about 4 wt. %; from 0.01 wt. % to about 3.5 wt. %; from 0.01 wt. % to about 3 wt. %; from 0.01 wt. % to about 2.5 wt. %; from 0.01 wt. % to about 2.25 wt. %; from 0.01 wt. % to about 2 wt. %; from about 0.01% to about 4 wt. %; from about 0.01 wt. % to about 3 wt. %; from about 0.01 wt. % to about 2.5 wt. %; from about 0.01 wt. % to about 2.25 wt. %; from about 0.01 wt. % to about 2 wt. %; from about 0.01 wt. % to about 1.5 wt. %; from about 0.01 wt. % to about 1 wt. %; from about 0.01 wt. % to about 0.5 wt. %; from 0.1 wt. % to about 10 wt. %; from 0.1 wt. % to about 9 wt. %; from 0.1 wt. % to about 8 wt. %; from 0.1 wt. % to about 7 wt. %; from 0.1 wt. % to about 6 wt. %; from 0.1 wt. % to about 5 wt. %; from 0.1 wt. % to about 4.5 wt. %; from 0.1 wt. % to about 4 wt. %; from 0.1 wt. % to about 3.5 wt. %; from 0.1 wt. % to about 3 wt. %; from 0.1 wt. % to about 2.5 wt. %; from 0.1 wt. % to about 2.25 wt. %; from 0.1 wt. % to about 2 wt. %; from about 0.1 wt. % to about 4 wt. %; from about 0.1 wt. % to about 3 wt. %; from about 0.1 wt. % to about 2.5 wt. %; from about 0.1 wt. % to about 2.25 wt. %; from about 0.1 wt. % to about 2 wt. %; from about 0.1 wt. % to about 1.5 wt. %; from about 0.1 wt. % to about 1 wt. %; from about 0.1 wt. % to about 0.5 wt. %; from 0.25 wt. % to about 10 wt. %; from 0.25 wt. % to about 9 wt. %; from 0.25 wt. % to about 8 wt. %; from 0.25 wt. % to about 7 wt. %; from 0.25 wt. % to about 6 wt. %; from 0.25 wt. % to about 5 wt. %; from 0.25 wt. % to about 4.5 wt. %; from 0.25 wt. % to about 4 wt. %; from 0.25 wt. % to about 3.5 wt. %; from 0.25 wt. % to about 3 wt. %; from 0.25 wt. % to about 2.5 wt. %; from 0.25 wt. % to about 2.25 wt. %; from 0.25 wt. % to about 2 wt. %; from 0.25 wt. % to about 1.75 wt. %; from 0.7 wt. % to about 10 wt. %; from 0.7 wt. % to about 9 wt. %; from 0.7 wt. % to about 8 wt. %; from 0.7 wt. % to about 7 wt. %; from 0.7 wt. % to about 6 wt. %; from 0.7 wt. % to about 5 wt. %; from 0.7 wt. % to about 4.5 wt. %; from 0.7 wt. % to about 4 wt. %; from 0.7 wt. % to about 3.5 wt. %; from 0.7 wt. % to about 3 wt. %; from 0.7 wt. % to about 2.5 wt. %; from 0.7 wt. % to about 2.25 wt. %; from 0.7 wt. % to about 2 wt. %; from about 0.7 wt. % to about 4 wt. %; from about 0.7 wt. % to about 3 wt. %; from about 0.7 wt. % to about 2.5 wt. %; from about 0.7 wt. % to about 2.25 wt. %; from about 0.7 wt. % to about 2 wt. %; from about 0.7 wt. % to about 1.5 wt. %; from about 0.7 wt. % to about 1 wt. %; from 0.9 wt. % to about 10 wt. %; from 0.9 wt. % to about 9 wt. %; from 0.9 wt. % to about 8 wt. %; from 0.9 wt. % to about 7 wt. %; from 0.9 wt. % to about 6 wt. %; from 0.9 wt. % to about 5 wt. %; from 0.9 wt. % to about 4.5 wt. %; from 0.9 wt. % to about 4 wt. %; from 0.9 wt. % to about 3.5 wt. %; from 0.9 wt. % to about 3 wt. %; from 0.9 wt. % to about 2.5 wt. %; from 0.9 wt. % to about 2.25 wt. %; from 0.9 wt. % to about 2 wt. %; from about 0.9 wt. % to about 4 wt. %; from about 0.9 wt. % to about 3 wt. %; from about 0.9 wt. % to about 2.5 wt. %; from about 0.9 wt. % to about 2.25 wt. %; from about 0.9 wt. % to about 2 wt. %; from about 0.9 wt. % to about 1.5 wt. %; from about 0.9 wt. % to about 1 wt. %; from 1 wt. % to about 10 wt. %; from 1 wt. % to about 9 wt. %; from 1 wt. % to about 8 wt. %; from 1 wt. % to about 7 wt. %; from 1 wt. % to about 6 wt. %; from 1 wt. % to about 5 wt. %; from 1 wt. % to about 4.5 wt. %; from 1 wt. % to about 4 wt. %; from 1 wt. % to about 3.5 wt. %; from 1 wt. % to about 3 wt. %; from 1 wt. % to about 2.5 wt. %; from 1 wt. % to about 2.25 wt. %; from 1 wt. % to about 2 wt. %; from about 1% to about 4 wt. %; from about 1 wt. % to about 3 wt. %; from about 1 wt. % to about 2.5 wt. %; from about 1 wt. % to about 2.25 wt. %; from about 1 wt. % to about 2 wt. %; from about 1 wt. % to about 1.5 wt. %; from about 1.5 wt. % to about 10 wt. %; from about 1.5 wt. % to about 9 wt. %; from about 1.5 wt. % to about 8 wt. %; from about 1.5 wt. % to about 7 wt. %; from about 1.5 wt. % to about 6 wt. %; from about 1.5 wt. % to about 5 wt. %; from about 1.5 wt. % to about 4.5 wt. %; from about 1.5 wt. % to about 4 wt. %; from about 1.5 wt. % to about 3.5 wt. %; from about 1.5 wt. % to about 3 wt. %; from about 1.5 wt. % to about 2.5 wt. %; from about 1.5 wt. % to about 2.25 wt. %; from about 1.5 wt. % to about 2 wt. %; or in any other amount within any of the above ranges.

The presently described topical compositions may be free from a fragrance, gluten and/or a paraben.

The biocompatible topical compositions may also include known biocompatible carriers, excipients, fillers, and diluents are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, the contents of all of which are hereby incorporated by reference in their entirety.

These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990) and Remington's Pharmaceutical Sciences, 18th Ed., Mack Publishing Co., Easton, Pa. (1990), both of which are incorporated by reference herein in their entirety.

Methods of Treatment

Also provided herein are methods of using the biocompatible topical compositions herein for treating, preventing or ameliorating rosacea, a symptom thereof or a condition related thereto.

The methods of treating, preventing, ameliorating rosacea described herein may comprise or consist of topically administering one or more of the described biocompatible topical compositions to skin of a subject in need thereof.

Also provided is a method of treating, preventing or ameliorating a symptom associated with rosacea that may comprise or consist of topically administering one or more of the described biocompatible topical compositions to skin of a subject in need thereof. Symptoms, including signs, as defined herein above that may be treated, prevented or ameliorated include one or more sign or symptom including, for example, erythema, telangiectasia, abnormal skin texture, skin discoloration, excess sebum production, swelling of the skin, skin nodularities, red patches on the skin, desquamation, skin lesions, stinging/burning, flushing and/or dry/tight skin.

Further provided is a method of treating, preventing or ameliorating one or more sub-type of rosacea. The methods of treating, preventing or ameliorating one or more sub-type of rosacea may comprise or consist of topically administering one or more of the described biocompatible topical compositions to skin of a subject in need thereof. The sub-types that may be treated, prevented or ameliorated include, for example, erythematotelangiectatic rosacea, papulopustular rosacea, phymatous rosacea, ocular rosacea and/or granulomatous rosacea.

In addition all of the methods described herein further comprise or consist of administering one or more additional composition to the subject. The one or more additional composition may be a skin cleanser, an oral composition for treating skin, a sunscreen such as, e.g., an organic sunscreen, a moisturizing composition, an exfoliating composition such as, e.g., an exfoliating polish, a barrier protecting composition and/or an additional topical composition for treating, preventing or ameliorating rosacea, a symptom thereof or a condition related thereto such as, e.g., a topical formulation comprising salicylic acid or benzoyl peroxide.

The methods may also further comprise or consist of administering or providing one or more additional therapies, including an at home or office administered concomitant device or therapies. Examples of at home use devices include hand held ultrasound, devices for administering light (UV light therapies, red light therapies, laser therapies, and therapies utilizing intense non-coherent light sources, LLLT (low level laser or low level light therapy), LILT (low intensity light therapy), photobiostimulation, biostimulation (BIOS), photobiomodulation, photonic stimulation, photo-rejuvenation or the like) and/or electrical therapy based (electrophoresis, electrophoresis or the like). Non-limiting examples of office-administered therapies include any concomitant therapy administered under the supervision of a dermatologist or other professional skin care provider, such as administration of the topical composition utilizing a micro-needle technique.

Suitable micro-needle therapies include those using arrays of relatively small structures, sometimes referred to as micro-needles or micro-pins, for delivery and/or removal of therapeutic agents and other substances through the skin and other surfaces.

In addition, the methods described herein may also further include administering one or more homeopathic products to the subject. Homeopathic therapies are those in which very dilute form of an active substance is used to relieve similar symptoms in conditions resulting from different etiologies. Non-limiting examples of homeopathic products include over the counter compositions comprising or consisting of one or more of topical or oral forms of *belladonna, nuxvomica*, sulphur, arsenicum alb., arsenicum bromatum, carbo animalis, causticum, hydrocotyle, kali brom., kali iod., kreosotum, lycopodium, nux vom., petroleum, rhustoxicodendron, sepia, sulphur, *echinacea, taraxacum, thuja occidentalis* leafy twig, pine needle oil (*pinus sylvestris*) *sambucus nigra* flower *calendula officinalis* flower, *abies balsamea* leaf oil, *echinacea angustifolia* or the like.

Dosage

The presently described biocompatible topical compositions can be topically administered in any form. A sufficient amount of the topical composition can be applied onto the affected area and surrounding skin, for example, in an amount sufficient to cover an affected area plus a margin of healthy skin or tissue surrounding the affected area, if possible, for example, a margin of about 0.5 inches. The compositions can be applied to any skin surface, including for example, facial skin, and the skin of the hands, neck, chest and/or scalp.

The compositions can be applied in a single, one-time application, once a week, once a bi-week, once a month, or from one to four times daily, for a period of time sufficient to alleviate symptoms, for example, for a period of time of one week, from 1 to 12 weeks or more, from 1 to 6 weeks, from 2 to 12 weeks, from 2 to 12 weeks, from 2 to 8 weeks, from 2 to 6 weeks, from 2 to 4 weeks, from 4 to 12 weeks, from 4 to 8 weeks, or from 4 to 6 weeks. The present compositions can be administered, for example, at a frequency of once per day or twice per day. The presently described compositions can be topically administered once per day for a period of time from 1 week to 4 weeks, of from 1 week to 2 weeks, for 1 week, for 2 weeks, for 3 weeks, for 4 weeks, or for 4 weeks or more.

The presently described topical compositions can be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24 hour period), can include, for example, from about 0.1 grams to about 6 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 1.5 grams; from about 0.5 grams to about 4.5 grams; 5 grams to about 4 grams; 0.5 grams to about 3.5 grams; 0.5 grams to about 3 grams; 0.5 grams to about 2.5 grams; 0.5 grams to about 2 grams; 0.5 grams to about 1 gram; about 0.5 grams; about 1 gram; about 1.5 grams; about 2 grams; about 2.5 grams; or about 3 grams.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The biocompatible compositions may be given in a single or multiple doses per time period, for example, daily, weekly, bi-weekly, or monthly. In an embodiment, the biocompatible compositions can be administered from one to four times per period, for example once daily or twice daily. In another embodiment, the present compositions may be administered once per week, for a period of from one to six weeks, for example for one week, for two weeks, for three weeks, for four weeks, five weeks, or for six weeks.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal topical biocompatible formulations will be determined by one skilled in the art depending upon considerations such as the particular active agent combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

The present biocompatible topical composition in accordance with the subject matter described herein may be a topical dosage form packaged in, for example, a multi-use or single-use package, including for example, a tube, a tottle, a pump, a container or bottle, a vial, a jar, a packet, or a blister package.

Single dosage kits and packages containing a once per day amount of the topical biocompatible composition may be prepared. Single dose, unit dose, and once-daily disposable containers of the present biocompatible compositions are contemplated as within the scope of the present subject matter.

The present topical biocompatible compositions remain stable in storage for periods including up to about 5 years, between about 3 months and about 5 years, between about 3 months and about 4 years, between about 3 months and about 3 years, and alternately any time period between about 6 months and about 3 years.

The presently described biocompatible topical composition in accordance with the subject matter described herein remains stable for up to at least 3 years at a temperature of less than or equal to 40° C. In an embodiment, the presently described topical formulation remains stable for at least 2 years at a temperature of less than or equal to 40° C. In an embodiment, the presently described biocompatible composition remains stable for at least 3 years at a temperature of less than or equal to 40° C. and at a humidity of up to 75% RH, for at least 2 years at a temperature of less than or equal to 40° C. and at a humidity of up to 75% RH, or for at least 3 years at a temperature of less than or equal to 30° C. and at a humidity of up to 75% RH. In a further embodiment, the presently described biocompatible composition in accordance with the subject matter described herein remains stable for an extended period of time when packaged in a multi-use container such as a bottle dispenser or the like, and exhibits equal to or even greater stability when packaged in a single-use package.

EXAMPLES

The following examples are illustrative of the present topical biocompatible compositions and are not intended to be limitations thereon.

Example 1

Table 1, shown below, is one example of a topical composition according to the present subject matter.

TABLE 1

| RAW MATERIAL | SUPPLIER | INCI | % W/W | AGENT FUNCTION |
| --- | --- | --- | --- | --- |
| Deionized Water | In-house | Water, Aqua, Eau | 69.9700 | Carrier/Solvent |
| Dissolvine Na2P | Akzo | Disodium EDTA | 0.0500 | Chelating Agent |
| Diglycerin 801 | US Cosmetics | Diglycerin | 3.0000 | Humectant |
| Keltrol CG | CP Kelco | Xanthan Gum | 0.3000 | Thickener |
| Xiameter 200 Fluid, 100 cs | Dow Corning | Dimethicone | 2.0000 | Skin Conditioning Agent |
| Kukui Nut Oil | Desert Whale | Aleurites Moluccan Seed Oil | 0.5000 | Emollient |
| Safflower Oil | Desert Whale | Carthamus Tinctorius (Safflower) Seed Oil | 0.5000 | Emollient |

TABLE 1-continued

| RAW MATERIAL | SUPPLIER | INCI | % W/W | AGENT FUNCTION |
|---|---|---|---|---|
| Lanette 16 | Cognis | Cetyl Alcohol | 2.0000 | Emulsifier,Thickener |
| Simulsol 165 | Seppic | PEG-100 Stearate (and) Glyceryl Stearate | 4.0000 | Emulsifier,Thickener |
| Permethyl 101A | Presperse | Isohexadecane | 1.7500 | Emollient |
| Beantree | Bernel | Methylheptyl Isostearate | 1.0000 | Emollient |
| Brij O20-SS | Croda | Oleth-20 | 0.3000 | Emulsifier |
| X-Pressin C | BASF | Water (and) Carbomer (and) Papain (and) 1,2 Hexanediol (and) Caprylyl Glycol, (and) Algin | 3.0000 | Exfoliating Agent |
| Neurocap | Codif/Barrnet | Hydrolyzed Algin | 2.2500 | Neurogenic Agent |
| Modukine | CLR | Lactose, Milk Protein | 1.2500 | Inflammatory Mgmt. Agent |
| Timecode | Seppic | Palmitoyl Glycine | 1.5000 | Vascular Repair Agent |
| Phytostem Edelweiss Marrubium Si-D Complex | Resources of Nature | Glycerin (and) *Leontopodium Alpinum* Meristem Cell Culture (and) *Marrubium Vulgare* Meristem Cell Culture, (and) Lecithin | 1.0000 | Antioxidant |
| Unitrienol T272 WSL | Induchem | PEG-12 Glyceryl Laurate, PEG-36 Castor Oil, Farnesyl Acetate, Farnesol, Panthenyl Triacetate | 2.5000 | Sebum Suppression Agent |
| Actiphyte of Broccoli Lipo Sun Special | Active Organics | *Brassica Oleracea Italica* (Broccoli) Extract (and) *Helianthus Annuus* (Sunflower) Seed Oil | 2.0000 | Anti-inflammatory Agent |
| Microkill COS | Arch | Phenoxyethanol (and) Caprylyl Glycol (and) Chlorphenesin | 1.0000 | Preservative |
| AMP Ultra PC-200 | Angus | Aminomethyl Propanol | 0.1300 | pH Adjuster |
| | | | 100.0000 | |

Example 2

Table 2, shown below, is another example of a topical composition according to the present subject matter.

TABLE 2

| RAW MATERIAL | SUPPLIER | INCI | % W/W | FUNCTION |
|---|---|---|---|---|
| Deionized Water | In-house | Water, Aqua, Eau | 72.3200 | Carrier/Solvent |
| Veegum Ultra | R.T. Vanderbilt | Magnesium Aluminum Silicate | 0.5000 | Thickener |
| Glycerine | Ashland | Butylene Glycol | 1.0000 | Solvent |
| Keltrol CG | CP Kelco | Xanthan Gum | 0.3000 | Thickener |
| Panthenol 50L | DSM | Panthenol | 2.0000 | Conditioning Agent |
| Dissolvine Na2P | Akzo | Disodium EDTA | 0.0500 | Chelating Agent |
| Xiameter 200 Fluid, 350 cs | Dow Corning | Dimethicone | 1.2000 | Skin Conditioning Agent |
| Lanette 16 | Cognis | Cetyl Alcohol | 2.0000 | Emulsifier,Thickener |
| Simulsol 165 | Seppic | PEG-100 Stearate (and) Glyceryl Stearate | 2.0000 | Emulsifier,Thickener |
| Amphisol K | DSM | Potassium Cetyl Phosphate | 1.0000 | Emulsifier |
| Minno 21 | Alzo/Bernel | Neopentyl Glycol Diethylhexanoate, Neopentyl Glycol Diisostearate | 1.5000 | Emollient, Skin-Conditioning Agent |
| Finsolv TN | Innospec | C12-15 Alkyl Benzoate | 1.5000 | Emollient |
| X-Pressin C | BASF | Water (and) Carbomer (and) Papain (and) 1,2 Hexanediol (and) Caprylyl Glycol, (and) Algin | 3.0000 | Exfoliating Agent |
| Neurocap | Codif/Barrnet | Hydrolyzed Algin | 2.2500 | Neurogenic Agent |
| Modukine | CLR | Lactose, Milk Protein | 1.2500 | Inflammatory Mgmt. Agent |
| Timecode | Seppic | Palmitoyl Glycine | 1.5000 | Vascular Repair Agent |
| Phytostem Edelweiss Marrubium Si-D Complex | Resources of Nature | Glycerin (and) *Leontopodium Alpinum* Meristem Cell Culture (and) *Marrubium Vulgare* Meristem Cell Culture, (and) Lecithin | 1.0000 | Antioxidant |
| Unitrienol T272 WSL | Induchem | PEG-12 Glyceryl Laurate, PEG-36 Castor Oil, Farnesyl Acetate, Farnesol, Panthenyl Triacetate | 2.5000 | Sebum Suppression |
| Actiphyte of Broccoli Lipo Sun Special *Helianthus Annuus* | Active Organics (Sunflower) | *Brassica Oleracea Italica* (Broccoli) Extract (and) Seed Oil | 2.0000 | Anti-inflammatory Agent |
| Microkill COS | Arch | Phenoxyethanol (and) Caprylyl Glycol (and) Chlorphenesin | 1.0000 | Preservative |

TABLE 2-continued

| RAW MATERIAL | SUPPLIER | INCI | % W/W | FUNCTION |
|---|---|---|---|---|
| AMP Ultra PC-2000 | Angus Chemical | Aminomethyl Propanol | 0.1300 | pH Adjuster |
| | | | 100.0000 | |

Example 3

Table 3, shown below, is yet another example of a topical composition according to the present subject matter.

TABLE 3

| RAW MATERIAL | SUPPLIER | INCI | % W/W | FUNCTION |
|---|---|---|---|---|
| Deionized Water | In-house | Water, Aqua, Eau | 46.3100 | Carrier/Solvent |
| Dissolvine Na2P | Akzo | Disodium EDTA | 0.0500 | Chelating Agent |
| Diglycerin 801 | US Cosmetics | Diglycerin | 3.0000 | Humectant |
| Keltrol CG | CP Kelco | Xanthan Gum | 0.3000 | Thickener |
| Xiameter 200 Fluid, 100 cs | Dow Corning | Dimethicone | 4.5000 | Skin Conditioning Agent |
| Kukui Nut Oil | Desert Whale | Aleurites Moluccan Seed Oil | 0.5000 | Emollient |
| Safflower Oil | Desert Whale | *Carthamus Tinctorius* (Safflower) Seed Oil | 1.0000 | Emollient |
| Lanette 16 | Cognis | Cetyl Alcohol | 3.7500 | Emulsifier,Thickener |
| Simulsol 165 | Seppic | PEG-100 Stearate (and) Glyceryl Stearate | 4.0000 | Emulsifier,Thickener |
| Permethyl 101A | Presperse | Isohexadecane | 1.7500 | Emollient |
| Beantree | Bernel | Methylheptyl Isostearate | 4.0000 | Emollient |
| Brij O20-SS | Croda | Oleth-20 | 0.3000 | Emulsifier |
| Dow Corning 9040 | Dow Corning | Cyclopentasiloxane (and) Dimethicone Crosspolymer | 10.0000 | Skin Conditioning Agent |
| Dow Corning 1501 | Dow Corning | Cyclopentasiloxane (and) Dimethiconol | 6.0000 | Skin Conditioning Agent |
| X-Pressin C | BASF | Water (and) Carbomer (and) Papain (and) 1,2 Hexanediol (and) Caprylyl Glycol, (and) Algin | 3.0000 | Exfoliating Agent |
| Neurocap | Codif/Barrnet | Hydrolyzed Algin | 2.2500 | Neurogenic Agent |
| Modukine | CLR | Lactose, Milk Protein | 1.2500 | Inflammatory Mgmt. Agent |
| Timecode | Seppic | Palmitoyl Glycine | 1.5000 | Vascular Repair Agent |
| Phytostem Edelweiss Marrubium Si-D Complex | Resources of Nature | Glycerin (and) *Leontopodium Alpinum* Meristem Cell Culture (and) *Marrubium Vulgare* Meristem Cell Culture, (and) Lecithin | 1.0000 | Antioxidant |
| Unitrienol T272 WSL | Induchem | PEG-12 Glyceryl Laurate, PEG-36 Castor Oil, Farnesyl Acetate, Farnesol, Panthenyl Triacetate | 2.5000 | Sebum Suppression |
| Actiphyte of Broccoli Lipo Sun Special | Active Organics | *Brassica Oleracea Italica* (Broccoli) Extract (and) *Helianthus Annuus* (Sunflower) Seed Oil | 2.0000 | Anti-inflammatory Agent |
| Sodium Hydroxide | Univar | Sodium Hydroxide | 0.0400 | pH Adjuster |
| Microkill COS | Arch | Phenoxyethanol (and) Caprylyl Glycol (and) Chlorphenesin | 1.0000 | Preservative |
| | | | 100.0000 | |

Example 4

In order to evaluate the effectiveness of present compositions a proof of principle clinical study was conducted on nine patients having varying skin types, of which were female and four of which were male. The study participants were between the ages of 32 and 78 years of age.

The participants each suffered from one or more sub-type of rosacea as described by Wilken et al. and characterized as shown in Table 4 below:

TABLE 4

| Rosacea Subtype | Characteristics |
|---|---|
| Erythemato-telangiectatic | Flushing and persistent central facial erythema with or without telangiectasia |
| Papulopustular | Persistent central facial erythema with transient, central facial papules or pustules or both |
| Phymatous | Thickening skin, irregular surface nodularities and enlargement May occur on the nose, chin, forehead, cheeks, or ears |

TABLE 4-continued

| Rosacea Subtype | Characteristics |
|---|---|
| Ocular | Foreign body sensation in the eye, burning or stinging, dryness, itching, ocular photosensitivity, blurred vision, telangiectasia of the sclera or other parts of the eye, or periorbital edema |
| Variant: granulomatous | Noninflammatory; hard; brown, yellow, or red cutaneous papules; or nodules of uniform size. |

The number of patients with diagnosed with each sub-type, as well as a breakdown of which patients suffered from each sub-type is as follows:
Erythematotelangiectatic=4 total, including Patient 2, Patient 3, Patient 4, and Patient 7;
Papulopustular=5 total, including: Patient 1, Patient 5, Patient 6, Patient 8, and Patient 9;
Phymatous=1 total—Patient 2;
Ocular=5 total, i.e., Patient 1, Patient 2, Patient 3, Patient 4, and Patient 8;
Granulomatous=0.
In addition to the above, the presence of flushing was observed in six patients, i.e., Patient 1, Patient 2, Patient 3, Patient 4, Patient 5, and Patient 6.

Study participants administered a topical composition according to Example 1-3 once-daily, for a period of 6 weeks. Patients were reviewed on a weekly basis. Clinical photographs (frontal, oblique) were obtained weekly and compared with baseline. Certain signs and symptoms specific to rosacea were graded by a physician weekly according to their change (−1=disimprovement, 0=no improvement, 1=minimal improvement, 2=moderate improvement, 3=significant improvement). An overall score was then generated for the observed changes in signs each week. The patient was simultaneously asked to grade changes in certain symptoms weekly. These were scored by the patient according to change (−1=disimprovement, 0=no improvement, 1=minimal improvement, 2=moderate improvement, 3=significant improvement). A total figure was generated for the changes in symptoms each week.

Over the course of the six-week period, all of the patients showed significant improvement in their rosacea. Physician graded signs improved to an overall score of 2.5/3, and patient graded symptoms to 2.9/3. The physician graded signs with the greatest improvement were texture (2.9/3), nodularities (2.8/3), sebum (2.7/3), erythema (2.5/3), telangiectasia (2.5/3), red patches/seborrheic dermatitis (2.3/3), desquamation (2/3), discoloration (1.4/3), and swelling (1.2/3). The patient graded symptoms with the greatest improvement included stinging/burning (2.8/3), flushing (2.3/3), and dryness/tightness (2.0/3).

Of particular note, the compositions yielded a dramatic improvement in overall lesion count. At baseline, there were 40 lesions tallied amongst all patients. By week 6, this has reduced to 13, representing a 68% improvement.

With regard to patients suffering from ocular rosacea, the patients with this disease subtype showed improvements in their patient graded signs symptoms (2.9/3) and physician graded signs (2.4/3). These included conjunctival hyperemia, pruritus, burning, dryness, lid inflammation, and periorbital edema. Of note, no signs or symptoms of rosacea deteriorated throughout the clinical study.

In addition, it should be noted that the environmental setting for the clinical trial afforded near 100% humidity levels. Of note, no patient complained of dryness, exfoliation, or discomfort while using the topical composition. Furthermore, no patient requested a "moisturizer" be added.

Remembering that rosacea occurs along a spectrum, patients who displayed more erythematotelangiectatic, phymatous, and ocular features received unexpectedly substantial benefits. Where the patient had a greater tendency towards the papulopustular subtype, improvement was clear, albeit not to as great a degree of patients suffering from erythematotelangiectatic, phymatous, and ocular subtypes.

Also of note, it is well documented that UV radiation is the premier trigger of rosacea in 81% of patients. Not unexpectedly, 88% of rosacea patients report a decrease in flares when they apply sunscreen. Sunscreen use was mindfully omitted from this Proof of Principle study, so as not to skew the results. It is however worth remembering, that the trial was carried out in Trinidad, the warmest Caribbean island. Furthermore, it was executed during the islands most arid period, the Dry Season. Surprisingly, while administration of the topical composition demonstrated superb results, all patients were still exposed to significant amounts of daily UV radiation throughout the study. This generated ongoing inflammation, barrier function disruption, and melanocyte activation amongst others. Naturally, this can limit the cumulative benefits of the composition, as the treatment was continually playing "catch-up" to the sun's ill-effects.

As described above and shown in Tables A-J below, administration of the topical compositions described herein yielded an excellent ability to treat, control, prevent and ameliorate of rosacea, a symptom thereof or a condition related thereto, over the six-week period. Tables A-J shown below includes the raw scores for each patient in the 9-patient cohort.

TABLE A

| Key |
|---|
| 0 Equals No Change |
| 1 Equals Minimal Change |
| 2 Equals Moderate Change |
| 3 Equals Significant Change |
| 4 Equals Not Applicable |
| 5 Equals Incomplete Data |

TABLE B

| Patient 1 | Week Number | | | | | | |
|---|---|---|---|---|---|---|---|
| | 0 | 1 | 2 | 3 | 4 | 6 | 7 |
| Signs/Symptom | Physician Graded | | | | | | |
| Erythema | 4 | 1 | 2 | 2 | 3 | 3 | 3 |
| Telangiectasia | 4 | 0 | 1 | 2 | 3 | 3 | 3 |
| Texture | 4 | 2 | 3 | 2 | 2 | 3 | 3 |
| Discoloration | 4 | 2 | 2 | 1 | 1 | 1 | 1 |
| Sebum | 4 | 2 | 2 | 2 | 2 | 3 | 3 |
| Swelling | 4 | 2 | 0 | 4 | 1 | 1 | 1 |
| Nodularities | 4 | Up by 2 | 0 | 3 | 2 | 3 | 3 |
| Red Patches | 4 | 0 | 4 | 4 | 4 | 4 | 4 |
| Desquamation | 4 | 0 | 4 | 4 | 4 | 4 | 4 |
| Lesion Count | 14 lesions | 6 lesions | 3 lesions | 3 lesions | 1 lesion | 4 | 2 |
| | Patient Graded | | | | | | |
| Stinging/Burning | 4 | 0 | 4 | 4 | 4 | 4 | 4 |
| Flushing | 4 | 1 | 2 | 3 | 3 | 3 | 3 |
| Dryness/Tightne | 4 | 0 | 4 | 4 | 4 | 4 | 4 |

TABLE C

| Patient 2 | Week Number | | | | | | |
|---|---|---|---|---|---|---|---|
| | 0 | 1 | 2 | 3 | 4 | 6 | 7 |
| Signs/Symptom | Physician Graded | | | | | | |
| Erythema | 4 | 2 | 2 | 5 | 3 | 3 | 3 |
| Telangiectasia | 4 | 1 | 1 | 5 | 3 | 3 | 3 |
| Texture | 4 | 3 | 2 | 5 | 3 | 3 | 3 |
| Discoloration | 4 | 2 | 2 | 5 | 2 | 2 | 2 |
| Sebum | 4 | 2 | 2 | 5 | 3 | 3 | 3 |
| Swelling | 4 | 1 | 2 | 5 | 3 | 3 | 3 |
| Nodularities | 4 | 0 | 0 | 5 | 4 | 4 | 4 |
| Red Patches | 4 | 2 | 2 | 5 | 3 | 3 | 3 |
| Desquamation | 4 | 1 | 2 | 5 | 3 | 3 | 3 |
| Lesion Count | 4 | 4 | 4 | 5 | 4 | 4 | 4 |
| | Patient Graded | | | | | | |
| Stinging/Burning | 4 | 4 | 0 | 5 | 3 | 3 | 3 |
| Flushing | 4 | 2 | 2 | 5 | 3 | 3 | 3 |
| Dryness/Tightne | 4 | 4 | 0 | 5 | 3 | 3 | 3 |

TABLE D

| Patient 3 | Week Number | | | | | | |
|---|---|---|---|---|---|---|---|
| | 0 | 1 | 2 | 3 | 4 | 6 | 7 |
| Signs/Symptom | Physician Grade | | | | | | |
| Erythema | 4 | 0 | 1 | 2 | 2 | 3 | 5 |
| Telangiectasia | 4 | 0 | 1 | 2 | 2 | 3 | 5 |
| Texture | 4 | 2 | 2 | 2 | 3 | 3 | 5 |
| Discoloration | 4 | 1 | 2 | 1 | 1 | 1 | 5 |
| Sebum | 4 | 2 | 2 | 2 | 3 | 3 | 5 |
| Swelling | 4 | 0 | 1 | 1 | 0 | 0 | 5 |
| Nodularities | 4 | 0 | 0 | 4 | 4 | 4 | 5 |
| Red Patches | 4 | 0 | 0 | 2 | 3 | 3 | 5 |
| Desquamation | 4 | 0 | 2 | 2 | 3 | 3 | 5 |
| Lesion Count | 3 lesions | 4 | 1 Lesion | 1 Lesion | 0 lesions | 0 | 5 |
| | Patient Grade | | | | | | |
| Stinging/Burning | 4 | 3 | 1 | 3 | 4 | 4 | 5 |
| Flushing | 4 | 1 | 2 | 2 | 3 | 3 | 5 |
| Dryness/Tightne | 4 | 4 | 2 | 2 | 3 | 3 | 5 |

TABLE E

| Patient 4 | Week Number | | | | | | |
|---|---|---|---|---|---|---|---|
| | 0 | 1 | 2 | 3 | 4 | 6 | 7 |
| Signs/Symptom | Physician Graded | | | | | | |
| Erythema | 4 | 0 | 5 | 3 | 2 | 2 | 3 |
| Telangiectasia | 4 | 0 | 5 | 2 | 3 | 3 | 3 |
| Texture | 4 | 3 | 5 | 3 | 3 | 3 | 3 |
| Discoloration | 4 | 2 | 5 | 2 | 1 | 1 | 1 |
| Sebum | 4 | 2 | 5 | 2 | 2 | 3 | 2 |
| Swelling | 4 | 0 | 5 | 2 | 4 | 4 | 4 |
| Nodularities | 4 | 0 | 5 | 2 | 4 | 3 | 3 |
| Red Patches | 4 | 0 | 5 | 4 | 4 | 4 | 4 |
| Desquamation | 4 | 0 | 5 | 4 | 4 | 4 | 4 |
| Lesion Count | 4 lesions | 4 | 5 | 1 lesion | 1 lesion | 3 | 2 |
| | Patient Graded | | | | | | |
| Stinging/Burning | 4 | 1 | 2 | 3 | 3 | 3 | 3 |
| Flushing | 4 | 0 | 0 | 2 | 1 | 3 | 2 |
| Dryness/Tightne | 4 | 1 | 4 | 4 | 4 | 4 | 4 |

TABLE F

| Patient 5 | Week Number | | | | | | |
|---|---|---|---|---|---|---|---|
| | 0 | 1 | 2 | 3 | 4 | 6 | 7 |
| Signs/Symptom | Physician Graded | | | | | | |
| Erythema | 4 | 1 | 2 | 5 | 2 | 1 | 3 |
| Telangiectasia | 4 | 0 | 2 | 5 | 2 | 1 | 3 |
| Texture | 4 | 2 | 2 | 5 | 3 | 3 | 3 |
| Discoloration | 4 | 1 | 1 | 5 | 0 | 0 | 0 |
| Sebum | 4 | 2 | 2 | 5 | 3 | 3 | 3 |
| Swelling | 4 | 1 | 0 | 5 | 0 | 4 | 4 |
| Nodularities | 4 | Worse | 0 | 5 | 3 | 3 | 3 |
| Red Patches | 4 | 1 | 0 | 5 | 3 | 3 | 3 |
| Desquamation | 4 | 1 | 0 | 5 | 2 | 2 | 2 |
| Lesion Count | 3 lesions | 1 Nodule | 1 lesion | 5 | 4 | 1 | 1 |
| | Patient Graded | | | | | | |
| Stinging/Burning | 4 | 1 | 1 | 5 | 2 | 3 | 2 |
| Flushing | 4 | 1 | 1 | 5 | 0 | 1 | 2 |
| Dryness/Tightne | 4 | 1 | 1 | 5 | 2 | 2 | 2 |

TABLE G

| Patient 6 | Week Number | | | | | | |
|---|---|---|---|---|---|---|---|
| | 0 | 1 | 2 | 3 | 4 | 6 | 7 |
| Signs/Symptoms | | | | | | | |
| Erythema | 4 | Worse | 2 | 2 | 2 | 2 | 2 |
| Telangiectasia | 4 | 0 | 0 | 2 | 2 | 2 | 2 |
| Texture | 4 | 2 | 2 | 3 | 3 | 3 | 3 |
| Discoloration | 4 | 2 | 2 | 2 | 2 | 2 | 2 |
| Sebum | 4 | 2 | 2 | 2 | 2 | 2 | 2 |
| Swelling | 4 | 2 | 2 | 1 | 1 | 1 | 1 |
| Nodularities | 4 | 0 | 2 | 2 | 3 | 2 | 2 |
| Red Patches | 4 | Worse | 2 | 1 | 2 | 1 | 2 |
| Desquamation | 4 | 0 | 0 | 0 | 0 | 0 | 0 |
| Lesion Count | 9 lesions | 7 | 4 Lesions | 4 | 1 lesion | 2 | 6 |
| | Patient Grade | | | | | | |
| Stinging/Burning | 4 | 0 | 4 | 2 | 4 | 4 | 4 |
| Flushing | 4 | 0 | 2 | 2 | 2 | 2 | 2 |
| Dryness/Tightne | 4 | 0 | 4 | 4 | 4 | 4 | 4 |

TABLE H

| Patient 7 | Week Number | | | | | | |
|---|---|---|---|---|---|---|---|
| | 0 | 1 | 2 | 3 | 4 | 6 | 7 |
| Signs/Symptom | Physician Grade | | | | | | |
| Erythema | 4 | 1 | 2 | 2 | 5 | 3 | 3 |
| Telangiectasia | 4 | 0 | 2 | 2 | 5 | 2 | 2 |
| Texture | 4 | 2 | 2 | 2 | 5 | 2 | 2 |
| Discoloration | 4 | 1 | 2 | 1 | 5 | 1 | 1 |
| Sebum | 4 | 2 | 2 | 2 | 5 | 2 | 2 |
| Swelling | 4 | 0 | 0 | 0 | 5 | 1 | 1 |
| Nodularities | 4 | 0 | 0 | 4 | 5 | 4 | 4 |
| Red Patches | 4 | 0 | 0 | 4 | 5 | 4 | 4 |
| Desquamation | 4 | 0 | 0 | 4 | 5 | 4 | 4 |
| Lesion Count | 4 | 0 | 4 | 4 | 5 | 0 | 0 |
| | Patient Grade | | | | | | |
| Stinging/Burning | 4 | 0 | 2 | 2 | 5 | 2 | 3 |
| Flushing | 4 | 0 | 0 | 4 | 5 | 0 | 0 |
| Dryness/Tightne | 4 | 0 | 0 | 4 | 5 | 0 | 0 |

TABLE I

| Patient 8 | 0 | 1 | 2 | 3 | 4 | 6 | 7 |
|---|---|---|---|---|---|---|---|
| Signs/Symptom | | | Physician Grade | | | | |
| Erythema | 4 | 1 | 5 | 2 | 5 | 3 | 3 |
| Telangiectasia | 4 | 1 | 5 | 2 | 5 | 3 | 3 |
| Texture | 4 | 1 | 5 | 2 | 5 | 3 | 3 |
| Discoloration | 4 | 1 | 5 | 2 | 5 | 3 | 3 |
| Sebum | 4 | 0 | 5 | 2 | 5 | 3 | 3 |
| Swelling | 4 | 0 | 5 | 2 | 5 | 4 | 4 |
| Nodularities | 4 | 0 | 5 | 3 | 5 | 3 | 3 |
| Red Patches | 4 | 0 | 5 | 1 | 5 | 2 | 2 |
| Desquamation | 4 | 0 | 5 | 1 | 5 | 2 | 2 |
| Lesion Count | 7 lesions | 6 lesions | 5 | 4 Lesions | 5 | 3 | 1 |
| | | | Patient Grade | | | | |
| Stinging/Burning | 4 | 0 | 5 | 4 | 5 | 4 | 4 |
| Flushing | 4 | 0 | 5 | 2 | 5 | 3 | 3 |
| Dryness/Tightne | 4 | 0 | 5 | 4 | 5 | 4 | 4 |

TABLE J

| Patient 9 | 0 | 1 | 2 | 3 | 4 | 6 | 7 |
|---|---|---|---|---|---|---|---|
| Signs/Symptom | | | Physician Grade | | | | |
| Erythema | 4 | 5 | 1 | 5 | 2 | 5 | 5 |
| Telangiectasia | 4 | 5 | 0 | 5 | 1 | 5 | 5 |
| Texture | 4 | 5 | 3 | 5 | 2 | 5 | 5 |
| Discoloration | 4 | 5 | 4 | 5 | 4 | 5 | 5 |
| Sebum | 4 | 5 | 3 | 5 | 2 | 5 | 5 |
| Swelling | 4 | 5 | 4 | 5 | 4 | 5 | 5 |
| Nodularities | 4 | 5 | 3 | 5 | 1 | 5 | 5 |
| Red Patches | 4 | 5 | 4 | 5 | 4 | 5 | 5 |
| Desquamation | 4 | 5 | 4 | 5 | 4 | 5 | 5 |
| Lesion Count | 38 | 5 | 5 | 5 | 16 | 5 | 5 |
| | | | Patient Grade | | | | |
| Stinging/Burning | 4 | 5 | 1 | 5 | 4 | 5 | 5 |
| Flushing | 4 | 5 | 4 | 5 | 4 | 5 | 5 |
| Dryness/Tightnes | 4 | 5 | 2 | 5 | 4 | 5 | 5 |

Figure 2:
FIG. 2 shows a side-by-side photographic comparison of another patient suffering from rosacea prior to and following six weeks of regular administration of the topical compositions described herein.

As a discussed, photographs were taken of all the patients during the study. The photographic evidence shows drastic improvement in all patients. For example, FIG. 1 is a side-by-side photographic comparison of Patient 4 prior to treatment, i.e., a baseline, and after six weeks of treatment. As shown, the patient's condition was markedly improved. Likewise FIG. 2, is a side-by-side photographic comparison of Patient 1 prior to treatment, i.e., a baseline, and after six weeks of treatment. As shown, the patient's condition was markedly improved.

All publications cited in the specification are indicative of the level of skill of those skilled in the art to which the presently described subject matter pertains. All of these publications are hereby incorporated by reference herein to the same extent as if each individual publication were specifically and individually indicated as being incorporated by reference.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A topical composition, comprising:
    an inflammatory management agent comprising lactose and/or milk protein, the inflammatory management agent being present in an amount of from about 0.01 wt. % to about 12.5 wt. % based on the weight of the topical composition;
    a vascular repair agent comprising palmitoyl glycine, the vascular repair agent being present in an amount of from about 0.01 wt. % to about 15 wt. % based on the weight of the topical composition;
    a neurogenic agent comprising an oligosaccharide, the neurogenic agent being present in an amount of from about 0.01 wt. % to about 22.5 wt. % based on the weight of the topical composition;
    a sebum suppression agent comprising Panthenyl Triacetate, farnesol and farnesyl acetate, the sebum suppression agent being present in an amount of from about 0.01 wt. % to about 25 wt. % based on the weight of the topical composition; and
    an exfoliating agent comprising at least one plant derived cysteine protease enzyme, the exfoliating agent being present in an amount of from about 0.01 wt. % to about 10 wt. % based on the weight of the topical composition.

2. The topical composition according to claim 1, further comprising one or more agent selected from the group consisting of a solvent, a chelating agent, a humectant, a thickener, emollient, an emulsifier, a skin conditioning agent, an antioxidant, an anti-inflammatory agent, pH adjuster and a preservative.

3. The topical composition of claim 1, wherein the inflammatory management agent is present in an amount of from about 0.25 wt. % to about 10.0 wt. % based on the weight of the topical composition.

4. The topical composition of claim 1, wherein the vascular repair agent is present in an amount of from about 0.25 wt. % to about 5.0 wt. % based on the weight of the topical composition.

5. The topical composition of claim 1, wherein the neurogenic agent is present in an amount of from about 0.1 wt. % to about 5.0 wt. % based on the weight of the topical composition.

6. The topical composition of claim 1, wherein the sebum suppression agent is present in an amount of from about 0.1 wt. % to about 5.0 wt. % based on the weight of the topical composition.

7. The topical composition of claim 1, wherein the exfoliating agent is present in an amount of from about 0.1 wt. % to about 10.0 wt. % based on the weight of the topical composition.

8. A topical dosage form selected from the group consisting of a cream, a lotion, an ointment, a foam, an aerosol, a powder, a solution, an emulsion, and a serum, comprising the topical composition according to claim 1.

9. The topical dosage form of claim 8, wherein the topical composition does not comprise a fragrance.

10. The topical dosage form of claim 8, wherein topical dosage form is a lotion.

11. A topical composition, consisting essentially of:
    an inflammatory management agent comprising lactose and milk protein, the inflammatory management agent being present in an amount of from about 0.01 wt. % to about 12.5 wt. % based on the weight of the topical composition;
    a vascular repair agent comprising palmitoyl glycine, the vascular repair agent being present in an amount of from about 0.01 wt. % to about 15 wt. % based on the weight of the topical composition;
a neurogenic agent comprising an oligosaccharide, the neurogenic agent being present in an amount of from about 0.01 wt. % to about 22.5 wt. % based on the weight of the topical composition;
a sebum suppression agent comprising Panthenyl Triacetate, farnesol and farnesyl acetate, the sebum suppression agent being present in an amount of from about 0.01 wt. % to about 25 wt. % based on the weight of the topical composition;
an exfoliating agent comprising at least one plant derived cystein protease enzyme, the exfoliating agent being present in an amount of from about 0.01 wt. % to about 10 wt. % based on the weight of the topical composition; and
optionally one or more agent selected from the group consisting of a solvent, a chelating agent, a humectant, a thickener, emollient, an emulsifier, a skin conditioning agent, an antioxidant, an anti-inflammatory agent, pH adjuster and a preservative.

12. A kit, comprising the topical composition of claim 1.

13. The kit of claim 12, further comprising one or more additional composition selected from the group consisting of a skin cleanser, an organic or an inorganic sunscreen, an exfoliating polish, a topical formulation comprising salicylic acid.

14. A method for treating rosacea, comprising:
topically administering a therapeutically effective amount of the topical composition according to claim 1 to skin of a subject in need thereof.

15. The method of claim 14, wherein the topical composition is a lotion.

16. The method of claim 14, wherein administering comprises twice daily application of the topical composition.

17. The method of claim 14, further comprising cleaning the skin prior to administration of the topical composition.

18. The method of claim 17, further comprising exfoliating the skin of the subject by administering an exfoliating polish.

19. The method according to claim 17, further comprising administering a topical formulation comprising salicylic acid to the skin of the subject.

20. The method according to claim 17, further comprising administering an organic or an inorganic sunscreen to the skin of the subject.

* * * * *